(12) United States Patent
Baier et al.

(10) Patent No.: US 7,209,547 B2
(45) Date of Patent: Apr. 24, 2007

(54) APPARATUS FOR SPATIAL MODULATION OF AN X-RAY BEAM

(75) Inventors: Florian Baier, Frankfurt (DE); Martin Hoheisel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 7 days.

(21) Appl. No.: 10/970,605

(22) Filed: Oct. 21, 2004

(65) Prior Publication Data

US 2005/0117707 A1   Jun. 2, 2005

(30) Foreign Application Priority Data

Oct. 21, 2003   (DE)   ................. 103 48 796

(51) Int. Cl.
*G21K 1/02*   (2006.01)
(52) U.S. Cl. ............ 378/149; 378/148; 378/150; 378/154
(58) Field of Classification Search ............ 378/2, 378/147–161; 310/328
See application file for complete search history.

(56) References Cited

U.S. PATENT DOCUMENTS

| | | | |
|---|---|---|---|
| 4,677,652 A * | 6/1987 | Duinker et al. ............. 378/151 |
| 4,715,056 A | 12/1987 | Vlasbloem et al. | |
| 4,741,012 A * | 4/1988 | Duinker et al. ............. 378/145 |
| 4,856,040 A * | 8/1989 | Geluk ........................ 378/146 |
| 5,044,007 A * | 8/1991 | Geluk et al. ................ 378/146 |
| 5,054,048 A | 10/1991 | Wang | |
| 5,067,144 A * | 11/1991 | Aitkenhead et al. ........ 378/146 |
| 5,210,782 A * | 5/1993 | Geluk et al. ................ 378/146 |
| 5,278,887 A | 1/1994 | Chiu et al. | |
| 5,365,140 A * | 11/1994 | Ohya et al. ................. 310/328 |
| 5,555,283 A * | 9/1996 | Shiu et al. .................. 378/151 |
| 6,377,661 B1 * | 4/2002 | Guru et al. ................. 378/149 |
| 6,442,238 B2 * | 8/2002 | Meulenbrugge ........... 378/98.8 |

(Continued)

FOREIGN PATENT DOCUMENTS

DE   94 09 376 U1   11/1995

(Continued)

OTHER PUBLICATIONS

Paolo Gaudenzi et al. Vibration Control of an Active Laminated Beam, 1997, Elsevier Science Inc., Composite Structures vol. 38, No. 1-4, pp. 413-420.*

(Continued)

*Primary Examiner*—Edward J. Glick
*Assistant Examiner*—John M. Corbett
(74) *Attorney, Agent, or Firm*—Schiff Hardin LLP

(57) ABSTRACT

An apparatus for spatial modulation of an x-ray beam has a number of planar attenuation elements for x-ray radiation that are disposed in a grid on a carrier and can be pivoted or tilted by a piezoelectric actuator, independently of one another, between at least two positions. One or more sensors with which a piezoelectrically-caused length and/or width and/or position change of the piezoelectrically influenced regions can be detected, are arranged on piezoelectrically influenced regions of the attenuation elements or the actuators. A significant dose reduction and/or dynamic adjustment thereof can be achieved with the apparatus by image adaptation in many areas of x-ray imaging, since a precise determination of the position of each attenuation element in real time is enabled.

22 Claims, 8 Drawing Sheets

U.S. PATENT DOCUMENTS

| | | | |
|---|---|---|---|
| 6,459,754 B1 * | 10/2002 | Besson et al. | 378/4 |
| 6,920,203 B2 * | 7/2005 | Short et al. | 378/147 |
| 2002/0003854 A1 * | 1/2002 | Ivan et al. | 378/20 |
| 2002/0015474 A1 * | 2/2002 | Tybinkowski et al. | 378/153 |
| 2003/0007601 A1 * | 1/2003 | Jaffray et al. | 378/65 |

FOREIGN PATENT DOCUMENTS

| | | |
|---|---|---|
| DE | OS 101 21 634 | 11/2002 |
| EP | 0 251 407 | 1/1988 |

OTHER PUBLICATIONS

Almon S. Shiu et al., Comparison of Miniture Multileaf Collimation (MMLC) with Circular Collimation for Steritactic Treatment, 1997, Elsevier Science Inc., Int. J. Radiation Oncology Biol. Phy., vol. 37, No. 3, pp. 679-688.*

* cited by examiner

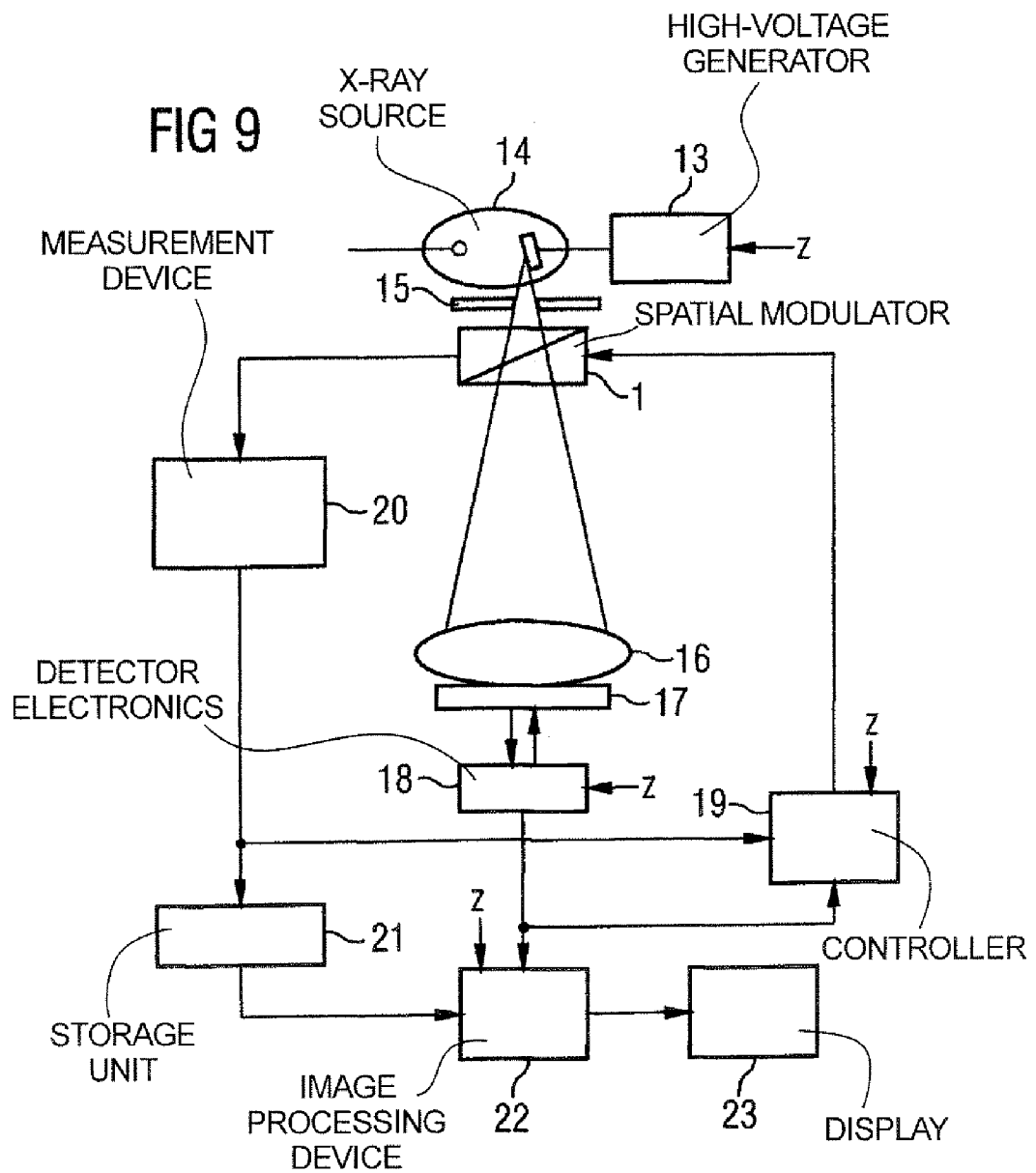

APPARATUS FOR SPATIAL MODULATION OF AN X-RAY BEAM

BACKGROUND OF THE INVENTION

1. Field of the Invention

The present invention concerns an apparatus for spatial modulation of an x-ray beam, of the type having a number of planar attenuation elements for x-ray radiation that are disposed in a grid-like manner on a carrier and that, independently of one another, can be pivoted or tilted piezoelectrically between at least two positions. The invention furthermore concerns an x-ray image system with such a modulation apparatus as well as different methods for operation of such an apparatus.

2. Description of the Prior Art

Laminar x-ray image systems are used primarily in medical diagnostics in order to acquire radiographic images of the inside of the body of a patient. The patient is penetrated by an x-ray field extending perpendicularly in two dimensions to the propagation direction, and the spatially dependent attenuation of the x-ray radiation received behind the patient is represented or evaluated as image information. In addition to conventional radiography, laminar x-ray imaging systems are used in fluoroscopy as well as, more recently, in so-called multi-slice systems in computed tomography.

The radiation dose to which the patient as well as the medical personnel is exposed during the examination plays a significant role in applications in medical x-ray diagnostics. A reduction of the applied x-ray dose can be achieved by use of a semi-transparent pre-filter that has a central opening for the unattenuated passage of x-ray radiation therethrough. By suitable placement of such a filter as is known, for example, from U.S. Pat. No. 5,278,887, only the region of the patient within the two-dimensional radiation field is charged with the necessary dose that is of interest for the user of the x-ray image system. The regions in the image lying outside of this ROI (region of interest) are nevertheless recognizable, albeit with reduced contrast. This technique in fact effects a significant dose reduction in the border regions of the image, but can be adapted only with difficulty to different subject shapes and sizes. Even with the use of such a filter technique, the dose at specific regions of the body to be examined is locally higher by multiple times more than would be necessary for a good contrast. This problem particularly occurs in body regions in which regions of much stronger x-ray absorption and regions of much weaker x-ray absorption lie next to one another. Since the diagnosing physician must normally examine all organs of an x-ray image, the applied x-ray dose is set such that a sufficient signal-to-noise ratio is achieved for all objects acquired in the image.

Apparatuses for spatial modulation of the radiation field that are positioned between the x-ray source and the patient are known in the field of x-ray imaging in which one-dimensional radiation fields are used in the form of fan-shaped x-ray beams for exposure such as, for example, in conventional computed tomography. In these apparatuses, for example, tongue-shaped attenuation elements are arranged in the form of a one-dimensional array corresponding to the one-dimensional extent of the radiation field. The attenuation elements can be controlled via separate actuators independently of one another, such that individual sections or channels of the one-dimensional radiation field can be weakened or modulated independently of one another by the introduction of the attenuation elements. Such an apparatus is known, for example, from U.S. Pat. No. 5,044,007, in which the attenuation elements are fashioned tongue-shaped and tiltable, and each can be tilted into the radiation field by its actuator. The control of the individual actuators ensues dependent on the x-ray radiation exiting from the body after irradiation of the body to be examined, relative to the respective channel that can be influenced with the attenuation element. The radiation dose necessary for a sufficient contrast can be locally reduced in this manner to the respectively necessary value, such that overall a reduced radiation exposure results for the patient.

Similar apparatuses are known from U.S. Pat. Nos. 5,054,048, and 4,715,056, and European Application 0 251 407. In U.S. Pat. No. 5,054,048, the attenuation elements are designed as sliding elements that are moved into or out of the beam by a sliding mechanism with an electromechanical drive. The attenuation elements are wedge-shaped, such that different degrees of attenuation can be achieved by displacement thereof perpendicular to the beam direction.

European Application 0 251 407 suggests the use of planar attenuation elements made from a piezoelectric material that can be tilted between two positions by the application of an electrical voltage.

From U.S. Pat. No. 4,715,056, a further one-dimensional attenuation apparatus is known in which tiltable pivotable planar attenuation elements are formed from a piezoelectric material as flex transducers that can be bent into the beam path by the application of an electrical voltage. This document furthermore discloses the possibility of an electromechanical drive as well as drive by means of a step motor. In the design with the electromechanical drive, the position of the attenuation elements is derived from the current strength of the current flowing through the electromagnet, namely the activating current.

A further apparatus for spatial modulation of a two-dimensional x-ray field is known from the German Application 102 21 634 (published after the priority date of the present application). In this apparatus, flex transducers (arranged in the form of a grid) to which self-supporting planar attenuation elements are attached, are aligned such that the attenuation elements stand in the beam direction. A minimal beam attenuation ensues in this position. By deflection of individual flex transducers via an electrical control, the attenuation at this location can be specifically increased. Knowledge of the position of each individual attenuation element during the image acquisition is necessary to damp the fluctuation behavior of the flex transducer and for image post-processing. The detection of the current position of each attenuation element ensues in this apparatus with an optical measurement arrangement that detects light passing through the grid of attenuation elements. For this purpose, a light source is necessary at the input side of the grid and a light deflection device is necessary at the output of the matrix. The respective positions of the attenuation elements are determined and evaluated by the shadowing thereof on a photodiode array caused by the attenuation elements. Errors can occur with such an optical detection due to light scattering and image blurring. Furthermore, light channels must be present in the grid mounting in order to be able to conduct the optical projection onto the photodiode array.

SUMMARY OF THE INVENTION

An object of the present invention is to provide an apparatus for spatial modulation of an x-ray beam by means of planar attenuation elements arranged in a grid, which enables a precise determination of the position of every attenuation element in real time.

The object is achieved by an apparatus according to the present invention having a number of planar attenuation elements for x-ray radiation disposed in a grid arrangement on a carrier, which can be pivoted or tilted piezoelectrically independently of one another between at least two positions. One or more sensors with which a piezoelectrically-caused length and/or width and/or position change of the piezoelectrically influenced regions can be detected are disposed on piezoelectrically influenced (in terms of length and/or width and/or position change) regions of the attenuation elements or piezoelectric drive elements that are connected with the attenuation elements.

The background for the present invention—as well as some of the apparatuses of the prior art—is the realization that the spatial distribution of the radiation field before the passage through the body of the patient is, aside from interference effects, practically homogenous, while as a consequence of the absorption ratios of the patent body the dynamic range in the radiation field immediately before the x-ray detector can amount to 1:1000 or greater. With the present apparatus, a further dose reduction is achieved because, within the two-dimensional radiation field before the passage through the body, a dose is applied that has an intensity no higher than is sufficient for a good contrast at this location to be obtained from the x-ray radiation that strikes the x-ray detector. The present apparatus thus enables a fast, adaptive, image-content-controlled spatial radiation attenuation in the two-dimensional radiation field in front of the patient body. The achievable dose reduction is based on individually applying, via controlled pivoting or tilting of the individual attenuation elements within their respective grid region (also designated in the following as a beam channel or cell), in each image region only as much of a dose as is necessary and that location to achieve a satisfactory signal-to-noise ratio.

The image signal acquired by the x-ray detector must be corrected dependent on the set spatial transparency of the apparatus operating as a radiation attenuator before further processing or display. For this, knowledge about the current position of each individual attenuation element during the image acquisition is necessary. In the present apparatus, this position information is obtained via the sensor signals that respectively detect the current flexing or expansion state of each individual attenuation element, or the piezoelectric actuation of the attenuation element, such that the exact position can be derived therefrom. This position is linked with the degree of attenuation of the respective channel, such that with this information an x-ray image acquired with the inventive apparatus can be normalized. The entire radiation distribution thus can be reverse calculated using the individual settings or deflection positions of the attenuation elements determined with the sensors.

In contrast to the aforementioned method for the determination of the position via the controller, the inventive solution offers the advantage of a higher degree of precision and, with respect to the technique of the subsequently published document, additionally offers the advantage of a smaller technical expenditure. By the inventive direct detection of the attenuation element, or its actuation element, no interfering signals of other attenuation elements occur, as with optical detection. Moreover, the attenuation elements or their piezoelectric drives can be completely glued at one end into the carrier serving as a mounting. This simplifies the production and leads to a higher stability of the mounting. The present invention enables the direct detection of the current position of each attenuation element in real time without the need for elaborate optics. Modifying influences, such as fluctuations and external interferences that can be individually different for each of the attenuation elements, also can be compensated.

The present apparatus can be particularly advantageously used in an x-ray image system in connection with a controller, with the position of a respective attenuation element currently detected with the sensor being compared with a reference position to be reached, and the attenuation element is controlled to reach the desired reference position. Naturally, it is not necessary for this purpose to concretely, spatially calculate the current position of the attenuation element. Rather, a known association between the sensor signal and the position of the attenuation element is sufficient, such that control can be based directly on the sensor signal.

In an embodiment of the present apparatus, the attenuation elements are themselves piezoelectric flex transducers attached on one side of the carrier. These flex transducers either can be formed directly from a material that strongly absorbs x-ray radiation, or can be coated with such a material such as, for example, tungsten.

In a further embodiment, the attenuation elements are formed as self-supporting elements, made of a material that strongly absorbs x-ray radiation, that are connected with piezoelectric drive elements. The piezoelectric drive elements are fashioned as piezoelectric flex transducers attached approximately parallel to the flex transducers on one side of the carrier, each having a free end to which the attenuation elements are attached. A "self-supporting attenuation element" as used herein means a component that is stable, in contrast to a thin layer, and can be arranged and moved freely in space without further support. A much larger movement range can be traversed in less time by a suitable arrangement of these self-supporting attenuation elements relative to the flex transducers. For example, planar metal rods or metal plates can be used as attenuation elements.

In an embodiment, the sensors for the detection of the piezoelectrically induced length and/or width and/or position change of the piezoelectrically influenced regions are tensiometer (strain gauge) strips that are attached to the flex transducers. These tensiometer strips directly detect the piezoelectrically caused expansion and thus the curvature of the flex transducer. The tensiometer strips can hereby either be glued or directly imprinted onto the flex transducer.

In a further embodiment, the sensors are directly integrated into the flex transducers. This ensues by the use of a further layer made of a piezoelectric material that is a component of the flex transducer. Such flex transducers are known, and are called trimorph flex transducers. This second layer made from a piezoelectric material is used as a sensor with which the respective current flexing of the flex transducer can be detected.

A carrier made from a material that optimally slightly absorbs the x-ray radiation to be modulated is used as a carrier or mounting in the preceding embodiments. In particular material made from plastic or a metal with a low atomic number are suitable.

In a further embodiment of the apparatus a substrate is used as the carrier, the substrate being penetrated by passage channels running parallel to one another or aligned to the focus of an x-ray source, with the attenuation elements being disposed in these channels. The attenuation elements are arranged such that they can be tilted or pivoted within the passage channels, such that each element completely closes (blocks) its channel in one position of the element. In this case, for each attenuation element two piezo-stack actuators can be provided as drive elements that are offset from one another on respective main surfaces of the attenuation element, and that are connected to the inner wall of the passage opening. In this embodiment, the attenuation elements can be tilted on a central axis given activation of the drive elements. The sensors are arranged on the piezo-stack actuators in order to detect their expansion. This can ensue, for with tensiometer strips.

In their neutral position, in which they attenuate the x-ray radiation the least within the cell or the beam channel, the longitudinal axis of each attenuation element is aligned to the focus of the x-ray source of the x-ray image system in which the elements are used. Upon activation, these attenuation elements are tilted within their respective cells such that they occupy a larger portion of the cell cross-sectional area. Due to the grid-like arrangement of the individual attenuation elements, a grid of controllable beam channels is created. The grid does not need to be sub-divided nearly as finely as the grid of the laminar x-ray detector in the x-ray image system. Due to the proximity of the attenuation elements to the focus of the x-ray source, they are deliberately imaged out-of-focus on the x-ray detector. It is advantageous for the shadowing effect of adjacent attenuation elements to partially overlap on the x-ray detector, since in this manner a more spatially consistent shadowing is created. The control of the quantum flow of the x-ray radiation in each radiation channel ensues by the variation of the angle of inclination or tilt angle of the attenuation elements. When the attenuation element is aligned with its longitudinal axis exactly on the focus of the x-ray source, the absorption in the radiation channel is at a minimum. In this position, the maximum value of the radiation is allowed to pass in this channel. When the attenuation element is maximally pivoted or tilted, radiation attenuation ensues in a larger portion of the radiation channel. An effective width of the absorbing part of the attenuation element in the cell that is effective for the absorption of the x-ray radiation in the channel region, corresponding to 11.43 times the actual width of this absorbing part is obtained by tilting the attenuation element of 5° relative to the neutral position. Given a width of, for example, 125 μm, this yields an effective width of 1.5 mm for the attenuation of the x-ray radiation. From this, given an x-ray voltage of 50 to 80 keV, a quantum flow change >10–13 is obtained as an attenuation factor in the case of an attenuation element with an absorbing part made from tungsten. It is necessary for these elements to exhibit a high degree of radiation absorption in order to actually modulate the radiation, rather than merely harden it.

The present x-ray image system with the inventive apparatus for spatial modulation of the x-ray beam includes an x-ray source and a laminar x-ray detector on opposite sides of an examination volume in a known manner. The inventive apparatus is disposed at the side of the examination volume near the x-ray source, in the beam path of the x-ray radiation. Furthermore, the x-ray image system has a controller to control the attenuation elements of the apparatus, preferably dependent on the spatial distribution of the x-ray radiation striking the x-ray detector. With this controller, the attenuation elements can be electronically controlled dependent on the locally received x-ray radiation or on the image content so that a consistent signal-to-noise ratio is attained with an optimally low x-ray dose. As needed, the attenuation elements are set to allow a reduced quantum flow by partial tilting. The contrast reduction thereby effected can be compensated in the image reproduction chain, for example by digital post-processing, with the effective action of the attenuation elements being detected with sensors in real time in each channel. In the image post-processing, for each pixel of the x-ray detector the actual amplitude value is multiplied with the previously measured attenuation factor at this pixel. This attenuation factor can also be composed of the shadowing effect of a number of attenuation elements, since this shadowing effect can be partially overlapped on the x-ray detector by the arrangement of the attenuation elements near the x-ray source.

In an embodiment of the x-ray image system, the controller for the attenuation elements is integrated into a control loop in which the attenuation elements are controlled dependent on the measurement signals of the sensors to achieve the predetermined desired position. In this manner, even given scatterings or other influences individually acting on the attenuation elements or their drive elements, a reliable adjustment of the desired position can be achieved.

The present apparatus can be used for different tasks in the field of x-ray imaging technology. In one application, the present application can serve for dose reduction, dynamic increase and/or improvement of the image quality in radiography exposures or DSA. In this application, the quantum flow is determined in the effective region by a two-dimensional x-ray detector (for example a solid-state detector) with fast sampling rate. The attenuation of the individual cells of the apparatus is detected during a first part of the exposure and the control unit uses this information for the adjustment of the attenuation of the individual channels. Higher intensity locations in the image receive fewer or no further quanta in the further exposure by reduction of the transparency by means of the beam attenuators in the second part of the exposure, while the attenuation elements remain set to the highest transparency at dark, low-intensity image locations. This application can be implemented in real time by means of the fast pivoting or tilting capability.

In this application of the apparatus, a significantly smaller x-ray dose is applied in relatively transparent image regions. The factor of the achievable dose reduction is subject-dependent and can be more than a factor of 10 in an individual case. Given implementation of this application with the use of additional pre-scans, the image acquired with the pre-scan can be integrated into the end image, such that all applied x-ray quanta contribute to the end image. The reaction time of the individual radiation attenuators must be fast enough for this application and the sampling rate of the x-ray detector must be relatively high. Values from 100 ms up to 100 μs can be achieved as a reaction time of the radiation attenuator. The attenuation elements operate only in the in/out mode, meaning without the use of intermediate settings.

A further application field of the present apparatus in medical diagnostics concerns the dose reduction, dynamic increase and/or improvement of the image quality in fluoroscopy. In this application, the transparency of the preceding images is used as a basis for the adjustment of the individual attenuation elements of the apparatus. Since the image content of successive images for the most part differs only a little in fluoroscopy, relatively slowly reacting attenuation elements can be used. The use of the present apparatus in RBV-based systems is particularly advantageous since the decrease in the tip brightness in a significant area of the RBV input screen has a beneficial effect on the contrast in the output image. By the additional reduction of scatter radiation achieved with the use of the inventive apparatus, a lower-noise image results. If necessary, the buffered data of the radiation attenuation, meaning duration, location and degree of the attenuation, can be supplied to a digital image processor that normalizes the contrast over the entire image, as described above. In this application, the attenuation elements operate in intermediate settings (not just in/out) that can be optimally selected based on the information of the preceding images.

Multi-slice CT systems represent a further application field of the inventive apparatus. In contrast to conventional CT systems with a single-line detector for image acquisition, the current development trend is in the direction of laminar CT systems. Up to 256 CT slices are simultaneously acquired in such systems by laminar, two-dimensional x-ray detector arrays. The inventive apparatus likewise can be used in such a two-dimensional radiation field as already explained in connection with fluoroscopy applications. In CT systems, however, the absorption data continually change due to the continuous rotation of x-ray detector and focal spot of the x-ray tube. This change can be predicted to a certain extent from the data of the preceding images of the sinogram, such that the respective position of the attenuation elements can be established with suitable prediction electronics. In the simplest version, such prediction electronics assume that the registered translations of the image signals continue further in the preceding images in the sinogram. It is thereby possible to use the same strategies in the control of the attenuation elements as these have already been explained for dose reduction, dynamic increase and/or improvement of the image quality in connection with fluoroscopy. However, since no preceding image data exists at the start of the application, in this case a start condition can be attained, for example with a single pre-scan with reduced dose. By the use of the inventive apparatus in such CT devices, a significant dose reduction as well as an improved image quality result due to reduced scatter radiation intensity.

DESCRIPTION OF THE DRAWINGS

FIG. 9 shows an exemplary embodiment of an x-ray image system using the inventive apparatus.

DESCRIPTION OF THE PREFERRED EMBODIMENTS

Figure 1:
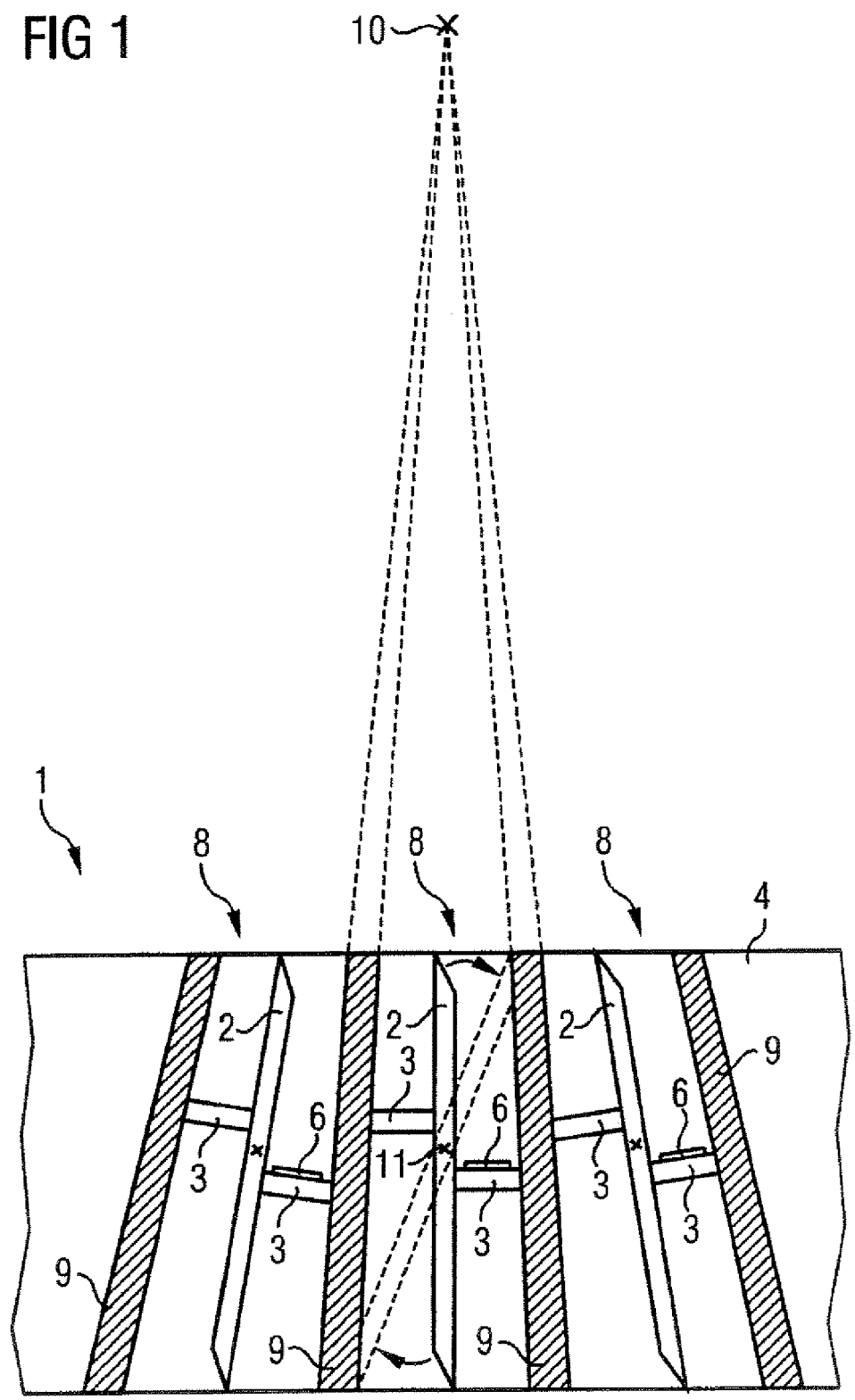
FIG. 1 is a schematic side view of a part of an exemplary apparatus according to the present invention.

FIG. 1 schematically shows a significantly enlarged section of an embodiment of the present apparatus disposed in the two-dimensional x-ray field of an x-ray image system. The apparatus 1 has a number of attenuation elements 2, arranged in a matrix or grid, that are connected to a carrier substrate 4 via piezoelectric drive elements 3. In this example, the carrier substrate 4 has a number of passage channels 8, with walls to which the drive elements 3 (fashioned as piezo-stack actuators in this example) are attached. Both the webs 9 forming the walls of the carrier 4 through which the passage channels 8 are established as cells and the attenuation elements 2 themselves are, in the rest position, aligned to the focal spot 10 of the x-ray tube, as is to the situation of FIG. 1. The surface of the carrier 4 alternatively can be fashioned in the form of a spherical surface instead of in the shown planar form, such that the x-rays originating from the focal spot 10 are incident perpendicularly at every location on this surface. The attenuation elements 2 are executed as flat paddles or plates of tungsten and each can be tilted around a virtual rotation axis 11 by means of the respective piezo-actuators 3. The actuators 3 responsible for each individual element 2 are arranged within the channel 8 such that they operate in the same direction. They simultaneously expand or simultaneously contract when a corresponding voltage is applied. Since the pair of actuators 3 for element 2 are offset with respect to the virtual rotation axis, the simultaneous expansion or contraction of the pair of actuators 3 tilts or pivots the element 2 as indicated by the curved arrows. The deflected position of the element 2 is shown dashed in the center cell of FIG. 1. In this tilted position, the maximum possible attenuation of x-ray radiation is achieved in the cell. By activation of the piezo-actuators 3 with a lower voltage, arbitrary intermediate positions can also be realized. The current positions of the respective piezo-actuators 3 and thus of the respective attenuation elements 2 is detected in this example by tensiometer strips 6 applied on the piezo-actuators 3. In the neutral position of the attenuation elements, as illustrated with the solid lines, the maximum possible portion of the x-ray radiation is allowed through the present apparatus. The material of the carrier 4 can be selected such that it absorbs x-ray radiation either very significantly or very weakly. In the first case, a fixed ratio of attenuation of the x-ray radiation must always be accepted, while in the second case the x-ray radiation through the apparatus cannot be completely blocked in the shown embodiment.

The elements 2 preferably are slanted at their end surfaces such that they lie flat against the walls of the webs 9, as shown by the dashed-line pivoted element 2 in FIG. 1. The x-ray radiation is optimally attenuated by this embodiment given a completely deflected element 2 in the passage channel 8.

Since the apparatus is designed for the activation of the drive elements 3 to operate in the same direction, the walls of the webs 9 can serve as electrical terminals (poles) for applying the voltage. The elements 2 thus do not have to be provided with electrical contacts. The contacting of the piezo-actuators 3 can be realized easily in this example, using thin metallic conductor runs on the webs 9 directly toward the edge of the apparatus in parallel or in a number of layers on one side of the carrier 4 while a common electrode is fashioned on the opposite surface of the carrier 4. The surface of the carrier 4 directed toward the side of the focal spot preferably carries the common electrode while the side of the carrier 4 facing away from the focal spot 10 carries the individual conductor runs, since a greater conductor run cross-section can be achieved on this side.

In this exemplary embodiment, multi-layer ceramics are used as the piezoelectric actuators 3 because these generate many times the excursion of single-layer ceramics. In order to reduce the requirements on the ceramic excursion in the present embodiment, the actuators 3 should act optimally close to the rotation axis 11, such that a small excursion of the actuators 3 effects a large displacement of the element 1 by lever action.

Figure 2:
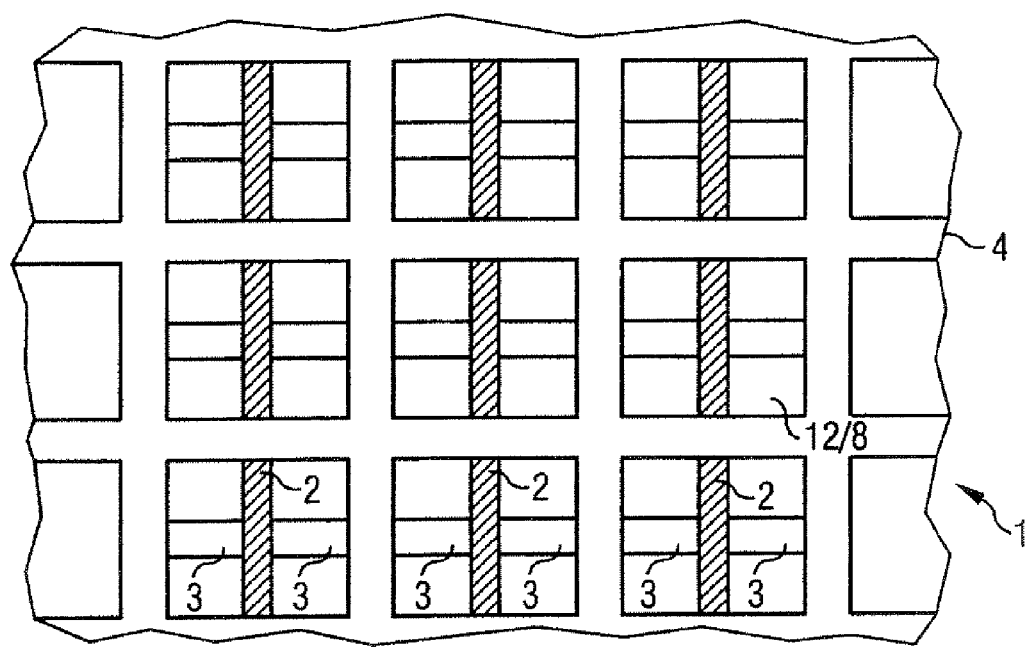
FIG. 2 is a plan view of an apparatus according to FIG. 1 in section.

The present apparatus has a number of attenuation elements 2, arranged in a grid, that the respective passage channels 8 of the carrier 4. In this manner, a matrix of controllable absorption cells 12 is formed as can be seen in section in the plan view in FIG. 2. FIG. 2 shows the webs of the carrier 4 that border the passage channels 8. Paddle-shaped attenuation elements 2 that are connected with the walls of the carrier 4 via the piezo-actuators 3 can be seen within the passage channels 8. The attenuation elements 2 are, in this example, held only the actuator elements 3.

Such an apparatus can be realized with any desired number of absorption cells 12. For example, a matrix can have 10×10 or 100×100 such absorption cells 12. Since a certain wall thickness of the webs 9 of the carrier 4 is necessary for the stability of the apparatus, it can be advantageous to arrange two or more such apparatuses in succession in the beam direction. A finer degree of spatial modulation of the beam profile is achieved by the multiple attenuation planes obtained in this manner. A particularly advantageous arrangement is achieved when the channels 8 of the two planes disposed in sequence influence are equally large quadratic solid angle of the focal spot 10 of the x-ray tube and are arranged such that one plane influences the light fields of a (theoretical) checkerboard pattern and the other plane influences the dark fields.

In an embodiment, the matrix or grid of the absorption cells 12 is disposed within the x-ray image system such that it faces the image matrix of the x-ray detector.

The individual attenuation elements 2 of the present apparatus are electronically controlled dependent on the image content of the regulating x-ray image so that a leveling of homogenization of the contrast in the x-ray image is effected. In lighter image regions, the beam attenuators 2 are set to effect a reduced quantum flow, meaning stronger attenuation, while the neutral setting is maintained in darker image regions. The contrast reduction thereby effected at the x-ray detector must be electronically compensated for the image reproduction. For this purpose, the angle setting of the attenuation elements 2 is detected in real time with the sensors 6 and the attenuation linked with the angle setting is used for normalization of the x-ray image.

Figure 3:
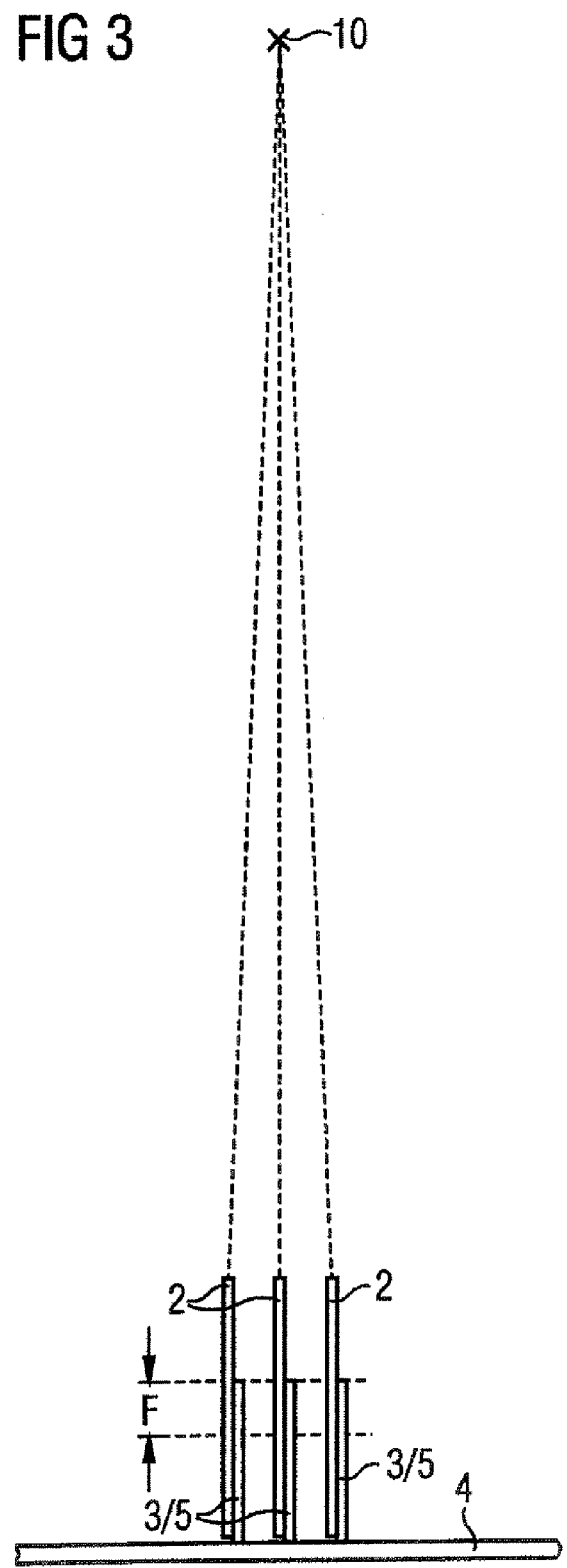
FIG. 3 shows, schematically in side view, three attenuation elements according to a further embodiment of the present invention that are in a neutral setting (position).
Figure 4:
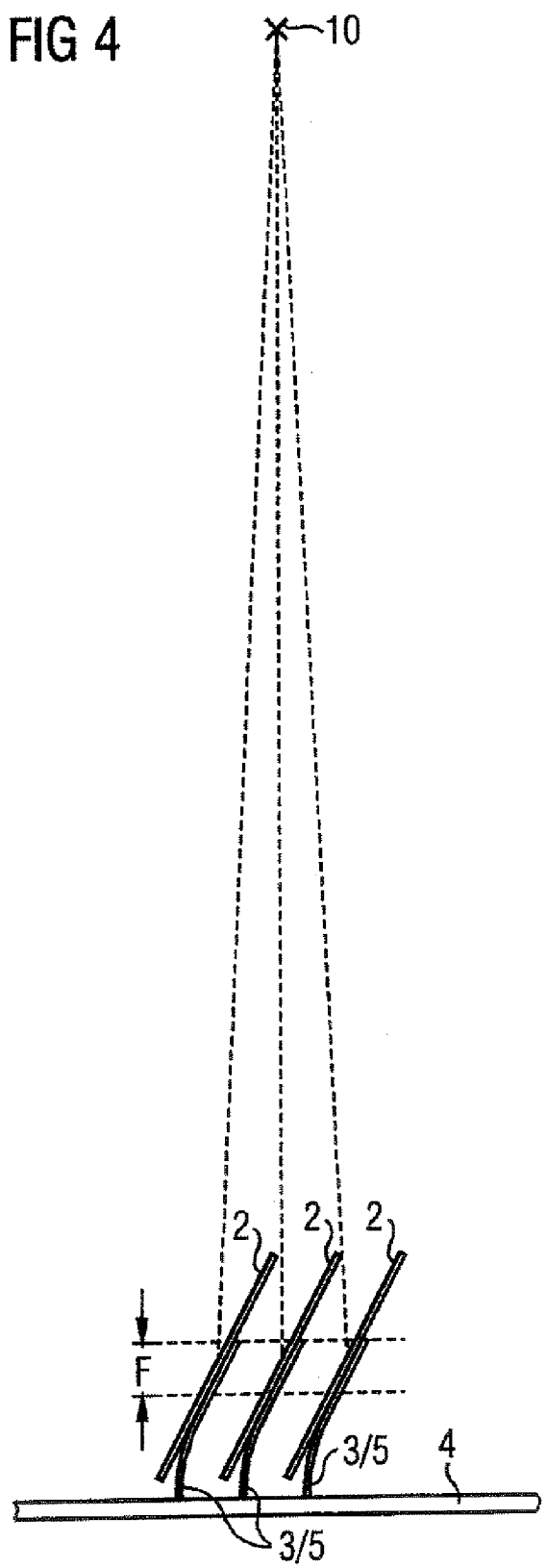
FIG. 4 shows the embodiment according to FIG. 3 in a deflected position of the attenuation elements.

An embodiment of the present apparatus is shown in FIGS. 3 and 4. Only three attenuation elements 2 are shown in side view in FIGS. 3 and 4, but naturally a larger number are present in the actual apparatus. FIG. 3 shows the arrangement of attenuation elements 2 on a (in this example) flat carrier substrate 4 made of a material transparent for x-rays, for example plastic. The carrier 4 alternatively can be spherical, such that the rays from the focal spot 10 of the x-ray tube always strike perpendicularly on the carrier surface. In the present embodiment, the piezoelectric drive elements 3 are executed as flex transducers 5 that are aligned in the direction of the focal spot 10 and stand on the carrier substrate 4. Each flex transducer 5 is preferably tongue-shaped or rod-shaped. The flat attenuation elements 2 that, in this example, are formed of tungsten and preferably exhibit a paddle or plate shape, are attached to the free ends of these flex transducers 5. The connection between the flex transducers 5 and the self-supporting attenuation elements 2 can be realized by gluing, pressing or soldering and only ensues in an end region of the flex transducer 5, which is indicated in FIGS. 3 and 4 with the reference character F. Each attenuation element 2 also forms an absorption channel of the apparatus together with the neighboring element 2.

Electrical contacting of the flex transducer 5 ensues on one or both surfaces of the carrier substrate 4, similar to that explained in connection with FIGS. 1, 2 and 3. FIG. 3 shows the neutral setting of the attenuation elements 2 in which these are aligned to the focus 10 of the x-ray tube. A corresponding sensor to detect the curvature (flexing) is mounted on each flex transducer 5, as explained in further detail using FIGS. 7 and 8. The sensors 6, 7 are not shown in FIGS. 3 and 4 (nor in FIGS. 5 and 6, in which they are also used.

Given an activation of the piezoelectric flex transducers 5, the attenuation elements 2 are tilted into the beam path of the x-ray radiation, as can be seen in FIG. 4. In this state, the entirety of the radiation is absorbed by the attenuation elements 2. The matrix-like arrangement of these attenuation elements 2 ensues in the same manner as explained in connection with FIGS. 1 and 2. In the embodiment of FIGS. 3 and 4, however, no passage channels are necessary in the carrier substrate 4 since the piezoelectric flex transducers 5 are arranged (with the attenuation elements 2 connected with them) directly on the surface of the substrate 4.

Figure 5:
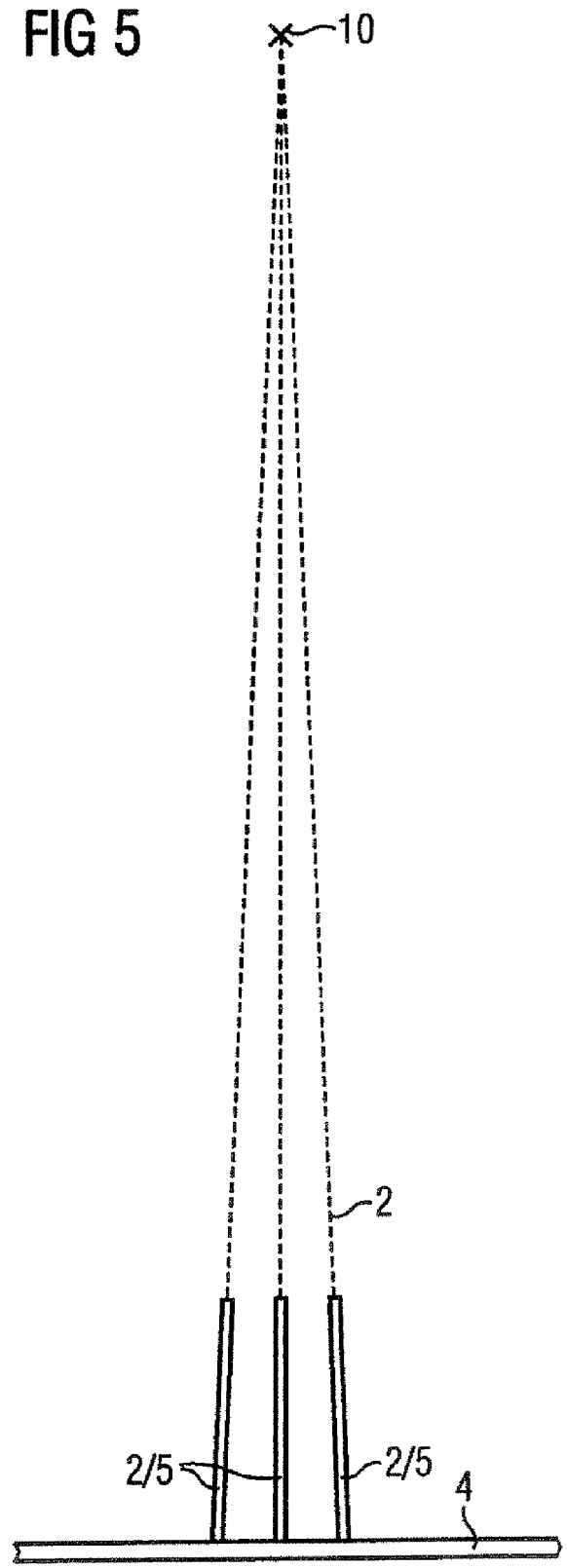
FIG. 5 shows, schematically in side view, three attenuation elements according to a further embodiment of the present invention that are located in a neutral Setting (position).
Figure 6:
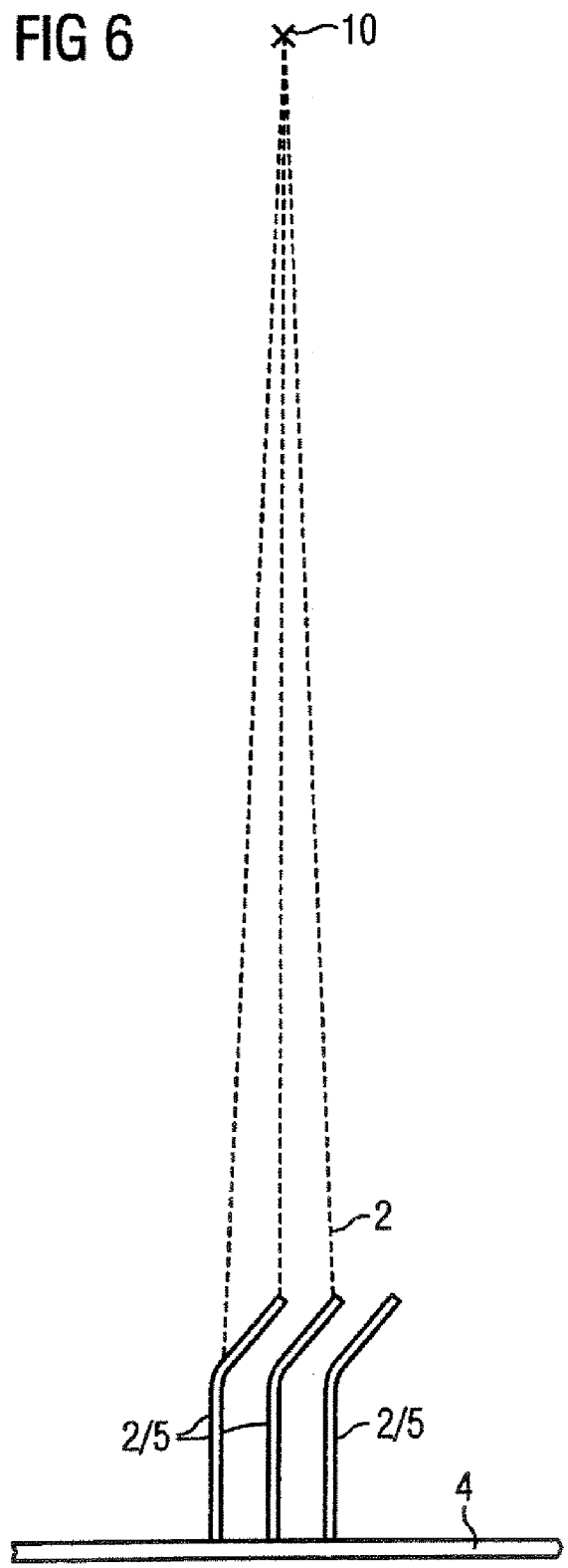
FIG. 6 shows the embodiment according to FIG. 5 with the attenuation elements in a deflected position.

FIGS. 5 and 6 show an embodiment of the inventive apparatus comparable to FIGS. 3 and 4, wherein in the attenuation elements 2 are directly fashioned as flex transducers 5. The flex transducers 5 can either be formed directly from a material that strongly absorbs x-ray radiation, for example lead zirconate titanate (PZT), lead metaniobate (PN) or lead nickel niobate (PNN), or can be coated with a layer of such a material, for example tungsten. Otherwise the same features as described in connection with FIGS. 3 and 4 are valid for FIGS. 5 and 6.

Figure 7:
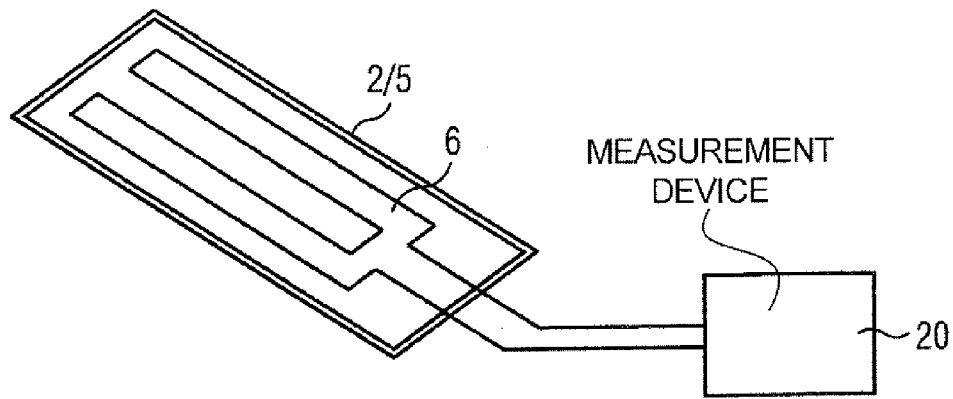
FIG. 7 shows an example for an attenuation element with an imprinted or glued-on tensiometer strip as a sensor.

FIG. 7 shows an example for a flex transducer 5 that can either be used as a piezoelectric drive element 3 for a self-supporting attenuation element 2 according to FIGS. 3 and 4, or directly as an attenuation element 2 according to FIGS. 5 and 6. At a region of the flex transducer 5 that is piezoelectrically influenced, meaning it can be mechanically varied by the application of an electrical voltage, a tensiometer strip 6 is attached with which the curvature of this flex transducer 5 can be detected by expansion or compression of the corresponding region. The tensiometer strip 6 can either be glued on or imprinted. The tensiometer strips 6 connected to measurement electronics 20 with which the deflection of the flex transducer 5 can be quantitatively determined.

Figure 8A:
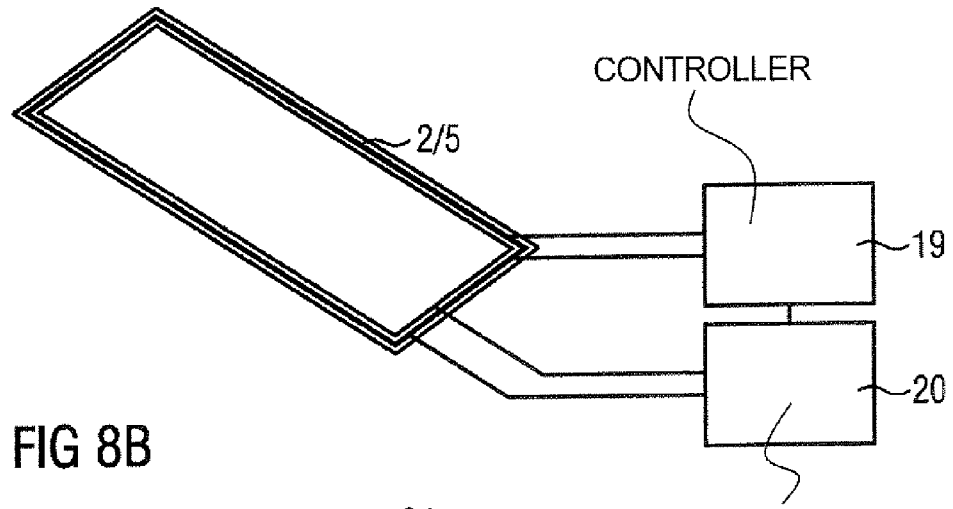
FIGS. 8A and 8B show further example of an attenuation element with an additional piezoelectric layer as a sensor.
Figure 8B:
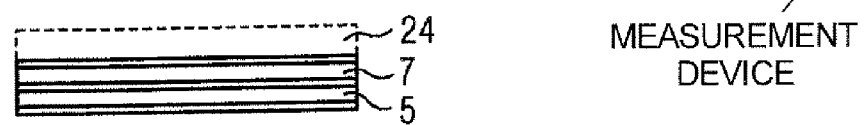

FIGS. 8A and 8B show a further example of such a flex transducer 5. In this embodiment, a double-layer flex transducer 5 is used, known as a trimorph flex transducer. With this transducer type, curvature is effected by application of an electrical voltage (via the controller 19) on the first layer of the flex transducer (the actuator). The second layer 7 of the flex transducer 5 serves as a sensor that emits a signal with which the curvature is quantitatively determined by the measurement electronics 20. FIG. 8A shows the basic embodiment of such a flex transducer 5 that, as in FIG. 7 as well, can be used either directly as an attenuation element 2 or as a piezoelectric drive element 3 for a self-supporting attenuation element 2. FIG. 8B shows (significantly schematized) the cross-section of such a flex transducer 5 with the additionally integrated piezoelectric layer 7 for the detection of the curvature. A coating 24 of a material that strongly absorbs x-ray radiation is indicated dashed. This coating is provided in the event that the flex transducer 5 is directly used as an attenuation element 2 and is not itself formed of material strongly absorbing x-ray radiation.

Furthermore, FIG. 8A shows an embodiment in which the curvature measured by the sensor and quantitatively determined by the measurement electronics 20 used in order to deflect each attenuation element to a desired degree in the form of a control loop. For this purpose, the measurement electronics 20 are connected to the controller 19 to form a control loop.

The apparatus described in the exemplary embodiments can be advantageously produced with techniques based on stereolithography. No tools or molds are necessary since changes as well as the design of these apparatuses can be realized on the software level. The carrier substrate in this case is formed of a polymer material, namely a suitably radiation-resistant polymer in order to achieve an acceptable lifespan of the apparatus. A further advantage of the technique of stereolithography for the production of the present apparatus is that the webs of the embodiment according to FIGS. 1 and 2 can be formed such that they are reinforced only where necessary for stability. The unwanted base absorption of the apparatus as well as undesirable radiation hardening due to the plastic body are thereby kept as low as possible.

FIG. 9 shows as an example an x-ray imaging system in which the inventive apparatus is used. In this system, the control of the attenuation elements 2 of the inventive apparatus 1 ensues according to the intensity distribution in the subject (the patient 16) determined in the detector output signal. FIG. 9 shows the high-voltage generator 13 for the operation of the x-ray tube 14. The patient 16 who is irradiated by the x-rays is positioned between the x-ray tube 14 and the x-ray image detector 17. A typical radiation diaphragm 15 to limit the radiation field as well as the inventive modulation apparatus 1 are disposed on the side near the x-ray tube. The intensity distribution within the image received by the detector 17 is evaluated by detector electronics 18. Given detection of lighter image locations, the attenuation elements are cell-selectively or channel-selectively activated by the controller 19 in order to reduce the dose in particular radiation channels. The position of the individual attenuation elements 22 within the apparatus 1 is detected and processed in real time with the measurement device 20 that is connected to the sensors 6, 7 of the attenuation elements 2, in order to provide the channel-dependent attenuation to a digital image post-processing 22 via a storage unit 21. The real value of the current attenuator setting is stored as a time curve in the storage unit 21. In this manner, the applied dose can be calculated for all pixels. The value for the exact reproduction (normalization) of the contrast values for the image representation of the x-ray image on the screen 23 can be derived from this information, the image representation being executed by digital image post-processing electronics 22. The image signal of pixels that (as a consequence of the setting of the attenuation elements 2) have received less quanta compared to others for which the attenuation elements are completely open (i.e. in the neutral position) is intensified corresponding to the calculated reduction of the quantum flow, thus increased in terms of contrast. The desired homogenous image impression results in this manner. The detected real values of the positions of the attenuation elements 2 can be simultaneously supplied to the attenuator controller 19 in order to form a control loop with which the position of the attenuation elements 2 can be exactly adjusted.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for spatially modulating an x-ray beam propagating in a beam direction and exhibiting a 2D radiation field, comprising:
    a carrier;
    a plurality of planar attenuation elements for x-ray radiation disposed in a 2D grid on said carrier substantially perpendicular to the beam direction and within said 2D radiation field each of said attenuation elements being a piezoelectric flex transducer having one end thereof fastened in said carrier;
    at least one piezoelectric actuator in mechanical engagement with each attenuation element for piezoelectrically displacing that attenuation element independently of all others of said attenuation elements to attenuate a portion of said x-ray beam in said 2D radiation field, the mechanically engaged attenuation element and piezoelectric actuator forming an element/actuator combination, and each of said attenuation elements and each of said actuators having a piezoelectrically influenced region exhibiting a piezoelectrically-caused change selected from the group consisting of a length change, a width change and a position change; and
    at each element/actuator combination, a sensor in mechanical contact with one of the piezoelectrically influenced regions of that element/actuator combination for detecting said piezoelectrically caused change and generating an electrical signal corresponding thereto.

2. An apparatus as claimed in claim 1 wherein said carrier is a substrate composed of material that is transparent to x-ray radiation.

3. An apparatus as claimed in claim 1 wherein said carrier comprises a substrate penetrated by a plurality of non-intersecting passage channels, with one element/actuator combination being disposed in each of said passage channels.

4. An apparatus as claimed in claim 3 wherein said passage channels are disposed parallel to each other in said carrier.

5. An apparatus as claimed in claim 3 wherein said x-ray radiation emanates from a focus, and wherein said passage channels are aligned in said carrier to said focus.

6. An apparatus as claimed in claim 3 wherein said attenuation elements are mounted in the respective passage channels so that a maximum of said piezoelectrically-caused position change causes the actuation element to completely close the passage channel in which it is disposed.

7. An apparatus as claimed in claim 3 wherein each of said passage channels has an inner wall, and wherein each of said attenuation elements has first and second oppositely disposed, substantially parallel primary surfaces, and wherein each element/actuator combination comprises one attenuation element and two piezoelectric actuators respectively disposed between said first and second primary surfaces and the inner wall of the passage channel in which the actuator/element combination is disposed, said two piezoelectric actuators being offset from each other for tilting the attenuation element around a central axis.

8. An apparatus as claimed in claim 7 wherein each of said piezoelectric actuators is a piezo-stack actuator.

9. An apparatus as claimed in claim 1 wherein each sensor is a tensiometer strip.

10. An apparatus as claimed in claim 1 wherein each of said attenuation elements is plate-shaped.

11. An apparatus as claimed in claim 1 wherein each attenuation element is comprised of a metallic material that strongly absorbs x-ray radiation.

12. An apparatus as claimed in claim 1 wherein each attenuation element comprises an element body coated with a metallic material that strongly absorbs x-ray radiation.

13. An apparatus for spatially modulating an x-ray beam propagating in a beam direction and exhibiting a 2D radiation field, comprising:
   a carrier;
   a plurality of planar attenuation elements for x-ray radiation disposed in a 2D grid on said carrier substantially perpendicular to the beam direction and within said 2D radiation field;
   at least one piezoelectric actuator in mechanical engagement with each attenuation element for piezoelectrically displacing that attenuation element independently of all others of said attenuation elements to attenuate a portion of said x-ray beam in said 2D radiation field, the mechanically engaged attenuation element and piezoelectric actuator forming an element/actuator combination, and each of said attenuation elements and each of said actuators having a piezoelectrically influenced region exhibiting a piezoelectrically-mused change selected from the group consisting of a length change, a width change and a position change;
   each of said attenuation elements being a self-supporting element and each of said piezoelectric actuators being a piezoelectric flex transducer, fastened at a first end thereof on said carrier and having an opposite second free end to which the attenuation element in the element/actuator combination is attached substantially parallel to the flex transducer; and
   at each element/actuator combination, a sensor in mechanical contact with one of the piezoelectrically influenced regions of that element/actuator combination for detecting said piezoelectrically caused change and generating an electrical signal corresponding thereto.

14. An apparatus as claimed in claim 13 wherein said carrier is a substrate composed of material that is transparent to x-ray radiation.

15. An apparatus for spatially modulating an x-ray beam propagating in a beam direction and exhibiting a 2D radiation field, comprising:
   a carrier;
   a plurality of planar attenuation elements for x-ray radiation disposed in a 2D grid on said carrier substantially perpendicular to the beam direction and within said 2D radiation field;
   at least one piezoelectric actuator in mechanical encasement with each attenuation element for piezoelectrically displacing that attenuation element independently of all others of said attenuation elements to attenuate a portion of said x-ray beam in said 2D radiation field, the mechanically engaged attenuation element and piezoelectric actuator forming an element/actuator combination, and each of said attenuation elements and each of said actuators having a piezoelectrically influenced region exhibiting a piezoelectrically-caused change selected from the group consisting of a length change, a width change and a position change;
   at each element/actuator combination, a sensor in mechanical contact with one of the piezoelectrically influenced regions of that element/actuator combination for detecting said piezoelectrically caused chance and generating an electrical signal corresponding thereto; and
   each element/actuator combination being formed as a flex transducer and each sensor comprising a piezoelectric layer integrated into the flex transducer.

16. An x-ray imaging system comprising:
   an x-ray source that emits an x-ray beam propagating in a beam direction and exhibiting a 2D radiation field;
   a laminar x-ray detector disposed in a path of said x-ray beam, said x-ray source and said x-ray detector defining an examination volume therebetween, said laminar x-ray detector emitting electrical signals dependent on said 2D radiation field incident thereon, collectively representing an x-ray image;
   a spatial modulator disposed in said x-ray beam at an x-ray source-proximate side of said examination volume, said spatial modulator comprising a carrier, a plurality of planar attenuation elements for x-ray radiation disposed in a 2D grid on said carrier substantially perpendicular to the beam direction and within said 2D radiation field, at least one piezoelectric actuator in mechanical engagement with each attenuation element for piezoelectrically displacing that attenuation element independently of all others of said attenuation elements to attenuate a portion of said x-ray beam in said 2D radiation field, the mechanically engaged attenuation element and piezoelectric actuator forming an element/actuator combination, and each of said attenuation elements and each of said actuators having a piezoelectrically influenced region exhibiting a piezoelectrically-caused change selected from the group consisting of a length change, a width change and a position change, and at each element/actuator combination, a sensor in mechanical contact with one of the piezoelectrically influenced regions of that element/actuator combination for detecting said piezoelectrically-caused change and generating an electrical signal corresponding thereto;
   a controller connected to each of said actuators for selectively displacing said attenuation elements independently of each other; and
   an image processing device supplied with the electrical signals from said laminar x-ray detector and the electrical signals from said sensors, said image processing device normalizing said x-ray image dependent on said signals from said sensors.

17. An x-ray imaging system as claimed in claim 16 comprising a control loop in which said controller is connected with the respective sensors and the respective actuators of each element/actuator combination, said controller using the electrical signal from the sensor for that element/actuator combination as a representation of an actual position of the attenuation element thereof, and controlling the piezoelectric actuator of that element/actuator combination to set the attenuation element thereof at a selected position.

18. An x-ray imaging system as claimed in claim 16 wherein said laminar x-ray detector emits electrical signals dependent on the x-ray radiation incident thereon, and wherein said controller is connected to said x-ray detector and receives the electrical signals therefrom, and controls actuation of the respective actuation elements dependent on the electrical signals from said laminar x-ray detector.

19. An x-ray imaging system as claimed in claim 18 wherein the electrical signals from said laminar x-ray detector collectively represent an x-ray image, and wherein said controller controls said actuators dependent on said electrical signals from said laminar x-ray detector to produce a maximum number of distinguishable grey scale values in said x-ray image.

20. An apparatus for spatially modulating an x-ray beam, comprising:
- a carrier comprising a substrate penetrated by a plurality of non-intersecting passage channels, each of said passage channels having an inner wall;
- a plurality of planar attenuation elements for x-ray radiation disposed in a 2D grid on said carrier, each of said attenuation elements having first and second oppositely disposed, substantially parallel primary surfaces;
- two piezoelectric actuators in mechanical engagement with each attenuation element for piezoelectrically displacing that attenuation element independently of all others of said attenuation elements, the mechanically engaged attenuation element and piezoelectric actuators forming an element/actuator combination, with one element/actuator combination being disposed in each of said passage channels of said carrier with the two piezoelectric actuators engaged therewith being respectively disposed between said first and second primary surfaces and the inner wall of the passage channel in which the actuator/element combination is disposed, said two piezoelectric actuators being offset from each other for tilting the attenuation element around a central axis; and
- at each element/actuator combination, a sensor in mechanical contact with one of the piezoelectrically influenced regions of that element/actuator combination for detecting said piezoelectrically caused change and generating an electrical signal corresponding thereto.

21. An apparatus as claimed in claim 20 wherein each of said piezoelectric actuators is a piezo-stack actuator.

22. An x-ray imaging system comprising:
- an x-ray source that emits x-ray radiation;
- a laminar x-ray detector disposed in a path of said x-ray radiation and emitting electrical signals dependent on said x-ray radiation incident thereon, said x-ray source and said x-ray detector defining an examination volume therebetween;
- a spatial modulator disposed in said x-ray radiation at an x-ray source-proximate side of said examination volume, said spatial modulator comprising a carrier, a plurality of planar attenuation elements for x-ray radiation disposed in a grid on said carrier, at least one piezoelectric actuator in mechanical engagement with each attenuation element for piezoelectrically displacing that attenuation element independently of all others of said attenuation elements, the mechanically engaged attenuation element and piezoelectric actuator forming an element/actuator combination, and each of said attenuation elements and each of said actuators having a piezoelectrically influenced region exhibiting a piezoelectrically-caused change selected from the group consisting of a length change, a width change and a position change, and at each element/actuator combination, a sensor in mechanical contact with one of the piezoelectrically influenced regions of that element/actuator combination for detecting said piezoelectrically-caused change and generating an electrical signal corresponding thereto;
- a controller connected to each of said actuators for selectively displacing said attenuation elements independently of each other; and
- an image processing device supplied with the electrical signals from said laminar x-ray detector and the electrical signals from said sensors, said image processing device normalizing said x-ray image dependent on said signals from said sensors.

* * * * *